US010016297B2

(12) United States Patent
Bue, Jr. et al.

(10) Patent No.: US 10,016,297 B2
(45) Date of Patent: Jul. 10, 2018

(54) NEUROMUSCULAR TRAINING DEVICE AND METHODS OF USE

(71) Applicant: TOPICAL GEAR, LLC, Austin, TX (US)

(72) Inventors: William Duane Bue, Jr., Austin, TX (US); Timothy Arlin Forsyth, Chandler, AZ (US)

(73) Assignee: Topical Gear, LLC, Lakeway, TX (US)

( * ) Notice: Subject to any disclaimer, the term of this patent is extended or adjusted under 35 U.S.C. 154(b) by 995 days.

(21) Appl. No.: 13/686,904

(22) Filed: Nov. 27, 2012

(65) Prior Publication Data
US 2013/0090585 A1 Apr. 11, 2013

Related U.S. Application Data

(63) Continuation-in-part of application No. PCT/US2011/038449, filed on May 27, 2011.

(60) Provisional application No. 61/349,157, filed on May 27, 2010.

(51) Int. Cl.
*A61F 5/00* (2006.01)
*A61F 5/02* (2006.01)

(52) U.S. Cl.
CPC .............. *A61F 5/028* (2013.01); *A61F 5/026* (2013.01)

(58) Field of Classification Search
CPC .. A61F 5/028; A61F 5/026; A61F 5/02; A61F 5/03; A61F 5/024; A61F 5/01; A61F 5/05808; A61F 5/24; A61F 5/088; A61F 5/05; A61F 5/37; A61H 1/0292; A41D 13/05; A41D 13/0512; A41D 13/0525; A41D 13/0531; A41D 13/0015; A41D 2400/32; A41D 13/0017; A63B 23/02; A63B 23/0233; A63B 23/0244; A63B 23/0205; A63B 2023/003; A63B 23/00; A63B 69/0059; A41B 1/08
USPC .......................................................... 602/19
See application file for complete search history.

(56) References Cited

U.S. PATENT DOCUMENTS

| | | | |
|---|---|---|---|
| 5,599,286 A | | 2/1997 | Labelle et al. |
| 5,776,087 A | * | 7/1998 | Nelson et al. |
| 6,440,094 B1 | | 8/2002 | Maas |
| 2004/0235581 A1 | * | 11/2004 | Citron et al. |
| 2006/0282032 A1 | * | 12/2006 | Smith et al. ................ 602/19 |
| 2009/0062704 A1 | | 3/2009 | Brown et al. |
| 2010/0010568 A1 | | 1/2010 | Brown |

OTHER PUBLICATIONS

International Search Report for PCT/US2011/038449 dated Sep. 28, 2011.

(Continued)

*Primary Examiner* — Victoria J Hicks
(74) *Attorney, Agent, or Firm* — Rodney J. Fuller; Booth Udall Fuller, PLC (57) ABSTRACT

The present invention is directed to a neuromuscular training device and methods of use. The device and methods are useful for enhancing the alignment of the upper torso of a user. The device preferably includes a scapular stabilization brace combined with a waist member anchored to the lower torso. The device is preferably configured specifically to provide scapular retraction and stabilization, while providing static and dynamic neuromuscular training.

20 Claims, 5 Drawing Sheets

(56) References Cited

OTHER PUBLICATIONS

Written Opinion of the International Searching Authority for PCT/US2011/038449 dated Sep. 28, 2011.
International Preliminary Report on Patentability for PCT/US2011/038449 dated Nov. 27, 2012.

* cited by examiner

NEUROMUSCULAR TRAINING DEVICE AND METHODS OF USE

CROSS-REFERENCE TO RELATED APPLICATIONS

This application is a continuation-in-part of International Application No. PCT/US2011/038449, filed May 27, 2011, which claims the benefit of U.S. Provisional Application No. 61/349,157, filed May 27, 2010, the contents of each of which are herein expressly incorporated by reference for all purposes.

BACKGROUND OF THE INVENTION

1. Field of the Invention

The present invention relates generally to methods and devices designed to enhance the alignment of the upper quadrant of a user's kinetic chain. More particularly, the methods and devices of the present invention utilize the benefits of scapular retraction and stabilization technology. The result is a novel, alignment-improving device, and method of use, comprised of a brace for the sacral, lumbar, and lower thoracic regions of the spine and a brace for scapular retraction and stabilization.

2. Discussion of the Background

Spine and Posture Generally

Proper alignment of the upper torso is associated with reduced incidence of back and spinal maladies. The spine (or backbone) runs from the base of the skull to the pelvis. Health professionals describe a healthy spine as having three natural curves. First, there should be an inward or forward curve at the neck (known as the cervical curve). Secondly, there should be an outward or backward curve at the upper back (known as the thoracic curve). And third, a healthy back will have an inward curve at the lumbar region of the spine (the lumbar curve). These natural curves give the spine an "S" shape when viewed from the side, and help the spine withstand great amounts of stress by providing a more even distribution of body weight. Proper alignment helps to maintain these natural curves, whereas poor alignment does the opposite—which may cause pain and result in stress, pulled muscles, or back injury.

There are numerous salutary effects associated with proper posture. For example, good posture keeps bones and joints in the proper alignment. This ensures that muscles are used properly, thereby decreasing the risk of musculoskeletal injury. Proper alignment also decreases the abnormal deterioration of joint surfaces, which, if left untreated, often results in arthritis. In addition, good posture reduces stress on the vital ligaments which hold the joints of the spine together. Proper alignment also precludes the spine from becoming fixed in an unhealthy, unnatural position. Muscles, moreover, are used more efficiently when one has a properly aligned upper torso, which allows the body to exert less energy. Furthermore, proper alignment reduces back strain and problems associated with overuse, and can prevent backaches and muscular pains. Finally, proper posture enhances one's outward appearance and has been associated with a heightened sense of well-being.

The spine is divided into three regions. From top (neck) to bottom, those regions consist of the cervical spine, the thoracic spine, and the lumbar spine, respectively. The neck comprises the uppermost portion of the spine. The seven vertebrae within this region (the cervical spine) are numbered C1 to C7 (from top to bottom). As noted above, the first spinal curve is located at the cervical spine. It resembles a "C" as it bends slightly inward—forming the curve which is also known as a lordotic curve. The 12 vertebrae (T1 to T12) below the cervical spine comprise the thoracic spine (within the chest section), to which the ribs attach. The thoracic spine provides the second spinal curve as it bends outward (like a backward "C"). This curve is termed the kyphotic curve. Next is the Lumbar spine (e.g. the lower back), consisting of five vertebrae (L1 to L5). Some individuals also have a sixth lumbar vertebra (L6). The lumbar spine has more than one vital function. Composed of the largest vertebrae, the lumbar spine interconnects the thoracic spine and the pelvis and supports the majority of the body's weight. Like the cervical spine, the lumbar spine also curves inward (creating a second lordotic curve) Immediately below the lumbar spine is a large bone known as the sacrum. The sacrum forms the base of the spine and the rear of the pelvis. The sacrum terminates at a small bone called the coccyx (or tailbone).

Role of the Scapula

Among the constellation of bones comprising the "upper extremity" of the human body is the shoulder girdle, which itself consists of the clavicle and scapula (or shoulder blade bone). The scapula is a large, flat, triangular bone, located at the rear of the rib cage at an upper left border. The scapula is capable of movement in several directions. Upwards (elevation) and downwards (depression), forwards (protraction) and backwards (retraction), in addition to circumduction (pivoting upward and outward or inward and downward over the posterior of the rib cage). Several muscles control these scapular movements, including the trapezius, pectoralis major and minor, and the rhomboids.

The scapula is an essential part of normal shoulder function. The scapulothoracic articulation accounts for approximately 30% of all shoulder motion, with the remaining 70% provided by the glenohumeral joint. There are 17 muscular attachments to the scapula. These muscles bring about complex movements of the scapula, including: elevation, depression, protraction, retraction, lateral rotation, medial rotation, upward rotation, downward rotation, anterior tipping, and posterior tipping. These movements demonstrate the complex nature of neuromuscular control of the scapula.

The scapula performs many roles, including glenohumeral articulation, facilitating movement along the thoracic wall, elevating the acromion (during overhead activities to clear the acromion from the moving rotator cuff) to avoid impingement and compression, and providing a critical link in the proximal to distal sequencing for shoulder function.

The scapula is pivotal in transferring significant forces and substantial energy from the legs, back, and trunk to the delivery point (the arm and hand), thereby allowing more force to be generated in activities such as throwing (than could be done by the arm musculature alone).

Scapular dyskinesia is the loss of normal scapular motion and mechanics. It is associated with numerous shoulder pathologies, including instability, labial tears, and rotator cuff disease. It is also associated with non-shoulder pathologies, such as excessive thoracic kyphosis, anterior chest contracture, nerve damage, and micro trauma. Although scapular dyskinesia is a known generator of shoulder pain and dysfunction, it is at best poorly understood or overlooked by most practitioners. Few health care providers have a functional grasp of this complex problem, and resources and modalities are limited to provide adequate treatment.

Scapular Stabilization

Existing and ongoing research indicates that proper positioning and dynamic stabilization of the scapula provides effective treatment for numerous maladies associated with the upper extremities (including the neck, shoulder, and upper trunk). At present, a rapidly expanding body of literature shows a correlation between abnormal scapular function (e.g. "scapular kinematics") and a variety of shoulder pathologies. (See *J Orthop Sports Phys Ther.* 2009 February 39(2): 90-104). Specifically, research now demonstrates a link between adverse scapular kinematic changes and shoulder impingement, rotator cuff tendinopathy, rotator cuff tears, glenohumeral instability, adhesive capsulitis, and stiff shoulders. Patients exhibiting these adverse scapular kinematic changes frequently suffer from reduced or altered functioning of the muscles that control scapula movement. For example, these patients often display reduced serratus anterior function and increased upper trapezius activation. In addition, scapular kinematic alterations often correlate with disfavored physiological conditions such as shortened rest length of the pectoralis minor, tight posterior shoulder, thoracic kyphosis, and flexed thoracic postures. All of the above pathologies emphasize the clinical and physiological importance of proper scapular positioning and stabilization. Despite this existing body of research, the science of scapular stabilization continues to evolve. Thus, current findings demonstrate the need for further investigation and for improved scapular stabilization devices that are capable of improving posture and ameliorating abnormal scapular kinematics.

Lumbar-Sacral Support, LSO Braces, and the Kinetic Chain

Scapular stabilization devices provide little or no support for the lumbar-sacral and lower thoracic region of the spine (e.g. the "lower back"). Lumbar sacral support reduces the load on the back muscles, and can be invaluable during episodes of acute and chronic lower back pain. Currently, patients in need of lower back support frequently turn to Lumbar-Sacral ("LSO") braces or other braces designed to support and/or stabilize the sacral, lumbar and lower thoracic region of the spine. Typically, LSO braces are indicated for Failed Lower Lumbar Surgery Syndrome, chronic low back pain, multiple level decompression, radiculopathy, and spinal stenosis, among other disorders. Common lower back braces encircle the lumbar-sacral region of the torso, and consist of anterior and posterior panels to provide rigid control of the spine/torso and enhance spinal alignment. When worn properly, LSO braces assist the patient's development of proper posture and muscle memory, thereby reducing the incidence of lower back pain and injury and improving spinal alignment.

Current LSO braces, however, do not address the need for scapular stabilization discussed above. Likewise, current scapular stabilization devices do not provide adequate lumbar-sacral support and stabilization. What is needed, therefore, is an improved orthopedic unit that combines the benefits of dynamic scapular stabilization with rigid control and support of the lumbar sacral region of the spine. The combination produces a synergistic—and not merely additive—effect. This appears to be due, at least in part, to the fact that the spine, scapula, and shoulder all comprise part of a common kinetic chain. Thus, spinal alignment has been shown to influence scapular position. Likewise, both scapular position and spinal alignment influence shoulder position. This kinetic chain, or dynamic interrelationship (between the spine, scapula, and shoulder), derives from at least two sources. First, there are numerous intermuscular connections between the spine, scapula, clavicle, and humerus. These muscular connections, therefore, exert functional control over the spine, scapula, and shoulder (relative to each other). Secondly, there is a well-recognized biomechanical model demonstrating integrated movement of the glenohumeral and scapulothoracic joints during scapular plane abduction (commonly termed "scapulohumeral rhythm").

One important study further demonstrated the critical interrelationship between the spine and scapula (and shoulder). In the study, researchers correlated slouched posture (as evidenced by an anterior tilt of the thoracic spine) with decreased scapular range of motion and increased anterior tilt (of the scapula). (See *Arch Phys med Rehabbil* 1999; 80:945-50). Conversely, the study demonstrated that bringing the thoracic spine posterior (indicative of proper posture) creates a corresponding posterior tilt (of the scapula), which in turn enhances humeral head alignment with the labrum to properly align the upper torso. As result, the researchers were able to conclude that thoracic spine position significantly affects scapular kinematics, and that slouched posture is associated with decreased muscle force.

SUMMARY OF THE INVENTION

The present invention is directed to a device for improving the upper torso alignment and methods of use. In a preferred embodiment the device includes a waist member and a scapular stabilization brace. The waist member typically has an inner and an outer surface, and opposing distal ends and includes a front side, a back side, and opposing lateral sides. The waist member is preferably configured such that when worn by the user the opposing distal ends are releasably secured to one another to anchor the waist member to and encircle the lower torso of the user. The scapular stabilization brace includes a garment configured to envelop at least a portion of the user's torso; the garment has a front side, and a back side. The front side of the garment includes a chest portion and the back side includes an upper back portion.

The scapular stabilization brace also preferably includes a pair of tension straps each affixed to opposing lateral sides of the upper back portion of the garment. While the garment is being worn by the user, each of the pair of tension straps diagonally extend toward opposing sides of the user's lower torso and through a pair of directional guide loops each disposed on the opposing lateral sides of the waist member and removably attached to the front side of the waist member.

According to an additional preferred embodiment, the waist member of the device may comprise a lumbar-sacral ("LSO") brace. The front side of the LSO brace includes an abdominal portion and the back side of the LSO brace comprises a sacral, lumbar and lower thoracic portion. The opposing distal ends of the LSO brace include fasteners releasably secured to one another in order to encircle the lower torso of the user and increase the compression applied to the user's lower torso.

According to an alternative preferred embodiment, the device includes a waist member that has a main body, an inner and an outer surface, and opposing distal ends, wherein when worn by the user, the waist member comprises a front side, a back side, and opposing lateral sides, and the opposing distal ends are releasably secured to one another in order to anchor the waist member to and encircle the lower torso of the user. The device also includes a scapular stabilization brace, wherein the scapular stabilization brace comprises a garment configured to envelop at least a portion of the user's torso, the garment having, a front side, and a back side. The front side of the garment comprises a chest portion and the back side of the garment comprises an upper back portion, a lower back portion, an inner garment layer, and an outer garment layer that substantially covers the inner garment layer. The scapular stabilization brace also includes a pair of tension straps each affixed to opposing lateral sides of the upper back portion of the inner garment layer and positioned between the inner garment layer and the upper back portion. While the garment is being worn by the user, each of the pair of tension straps preferably diagonally extends across the back of the user, toward opposing sides of the user's lower torso and through strap orientation members, disposed on the opposing lateral sides of the waist member and removably attached to the front side of the waist member.

BRIEF DESCRIPTION OF THE DRAWINGS

The accompanying drawings, described below, illustrate preferred embodiments of the present invention. It will be understood that no limitation to the scope of the invention is intended thereby. These drawings depict various features and further advantages of the present invention. The invention is not limited to the particular embodiments disclosed in these drawings, as it should be understood by one skilled in the art that additional features, modifications, and alternative embodiments are contemplated by the invention as disclosed herein.

DETAILED DESCRIPTION OF THE PREFERRED EMBODIMENTS

Figure 1:
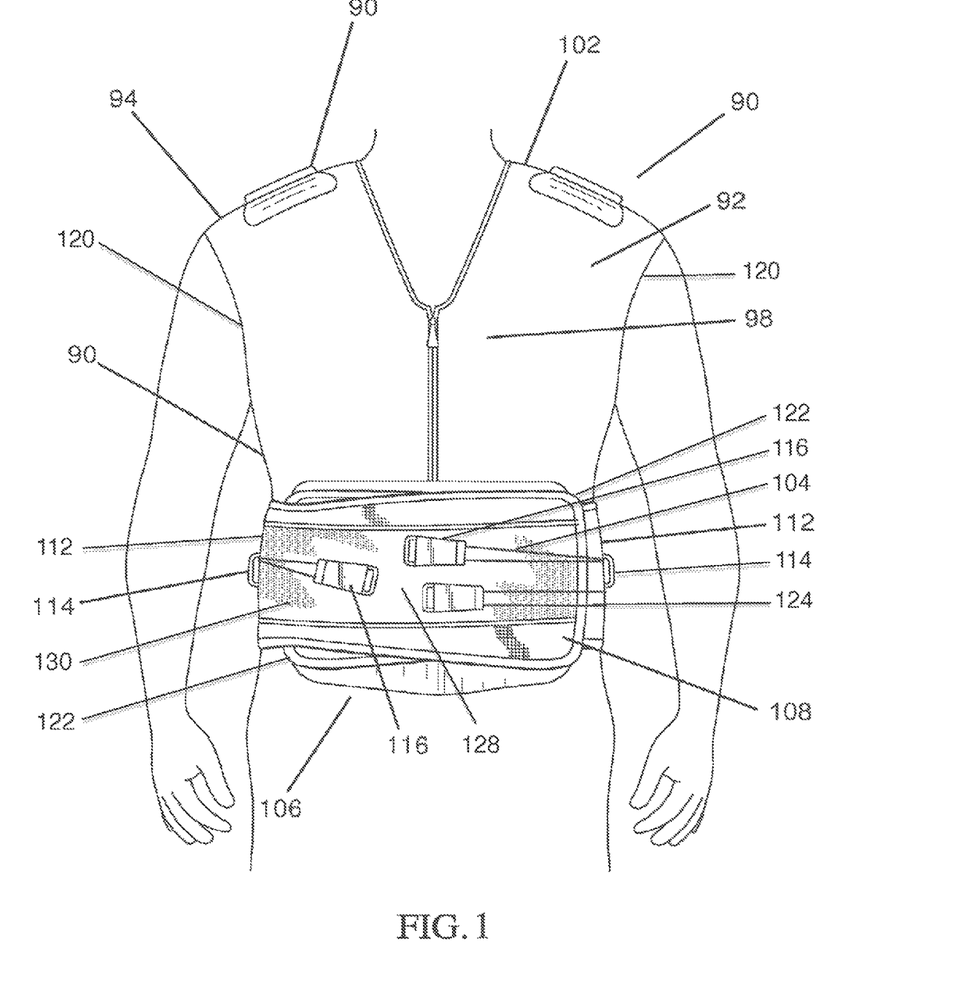
FIG. 1 is a front elevational view of an embodiment of the present invention.
Figure 2:
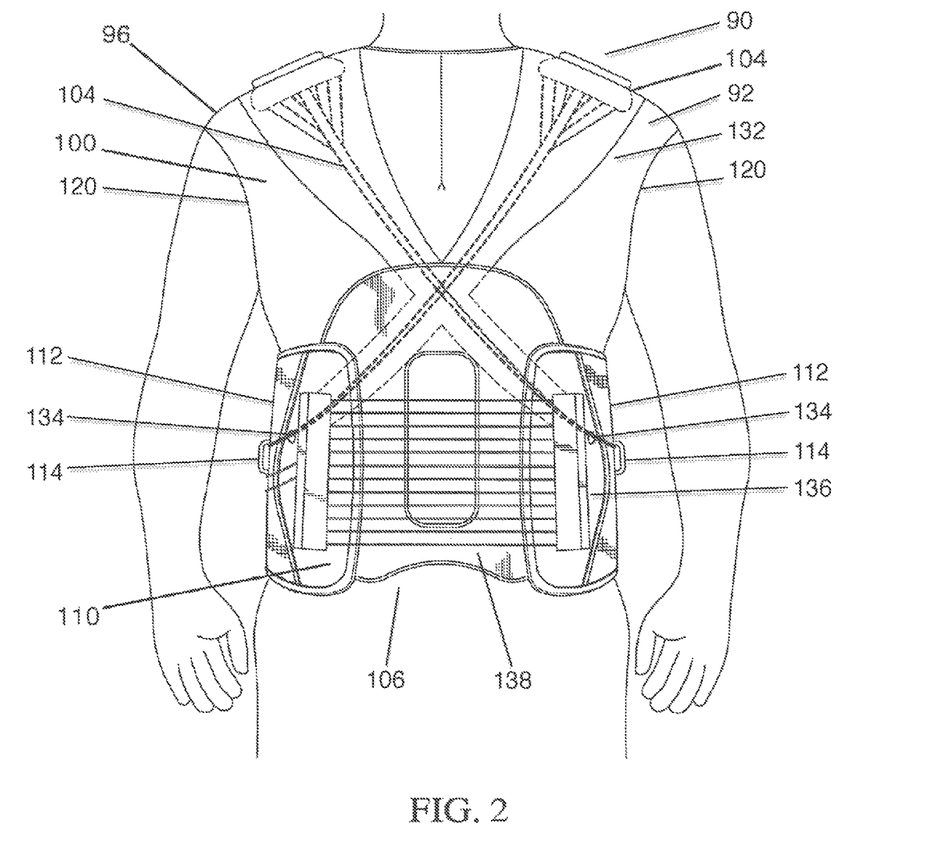
FIG. 2 is a rear elevational view of an embodiment of the present invention.
Figure 3:
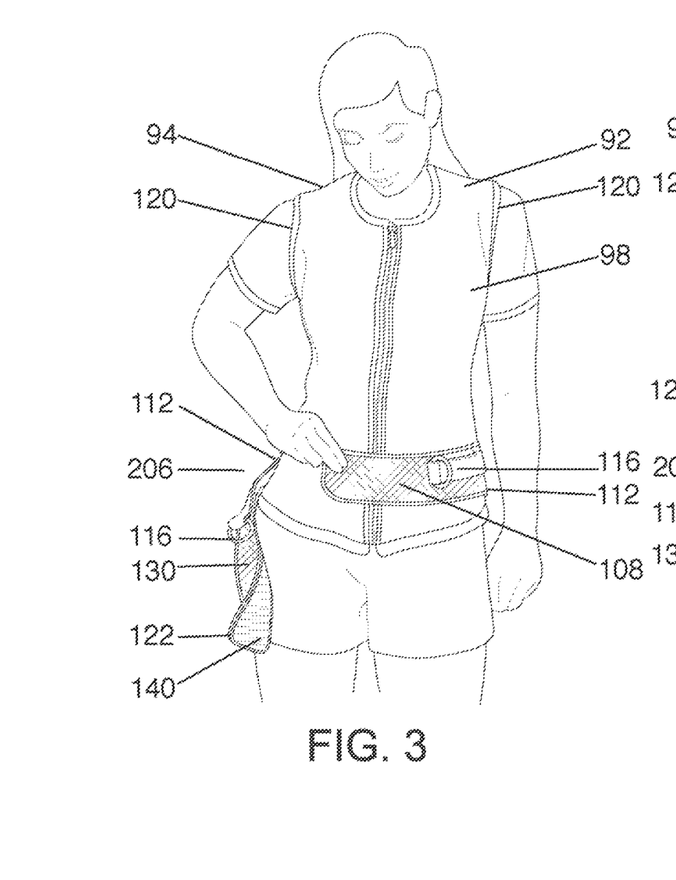
FIG. 3 is a front elevational view of an embodiment of the present invention, worn by a user prior to securing the waist member around the torso.
Figure 4:
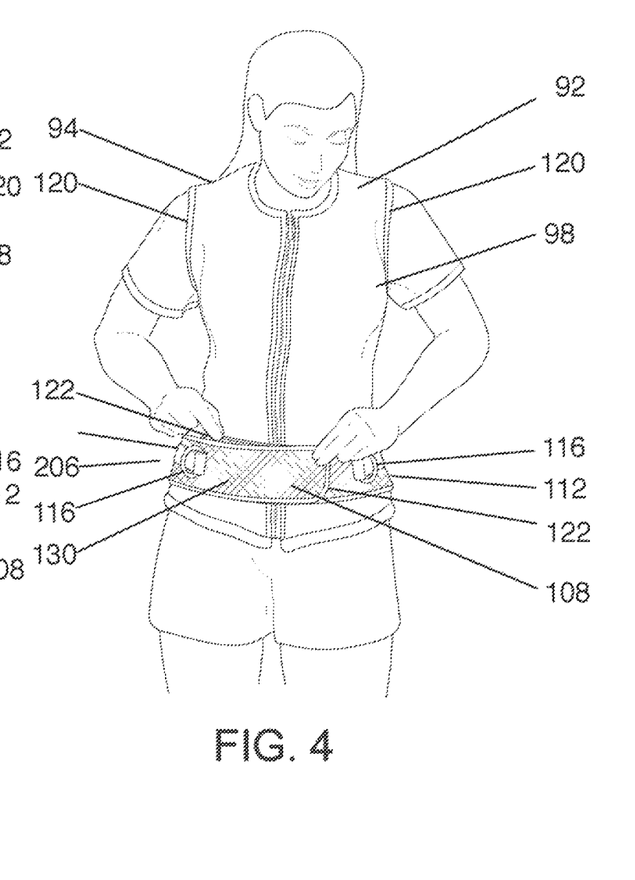
FIG. 4 is a front elevational view of an embodiment of the present invention, worn by a user while securing the waist member around the torso.
Figure 5:
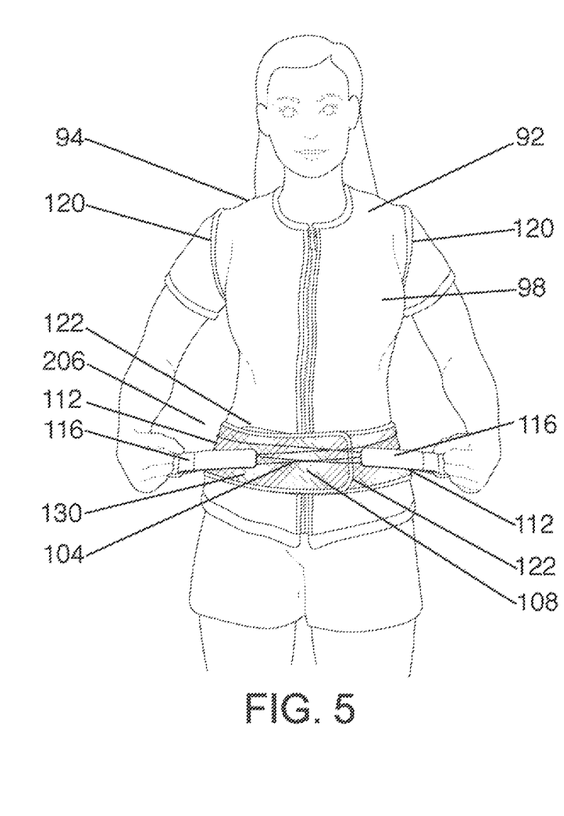
FIG. 5 is a front elevational view of an embodiment of the present invention, worn by a user while adjusting the scapular stabilization brace.
Figure 6:
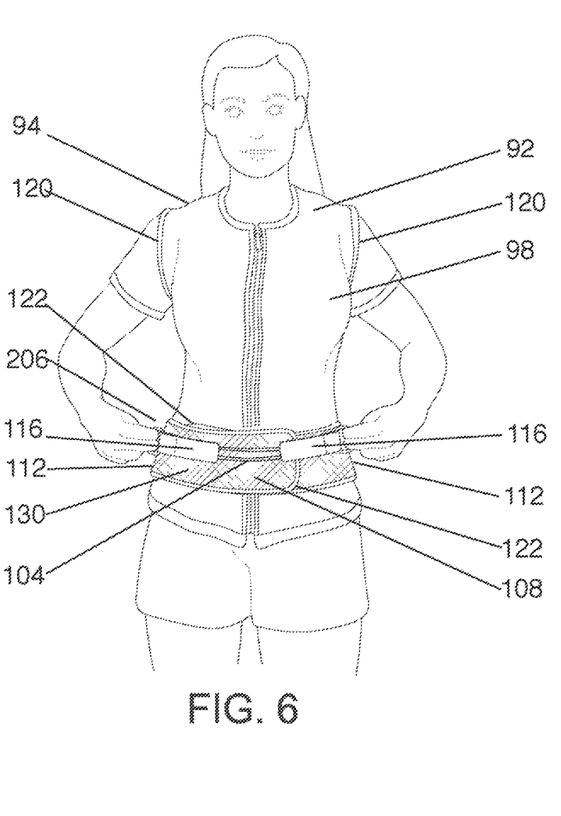
FIG. 6 is a front elevational view of an embodiment of the present invention, illustrating the waist member secured to the torso of a user.
Figure 7:
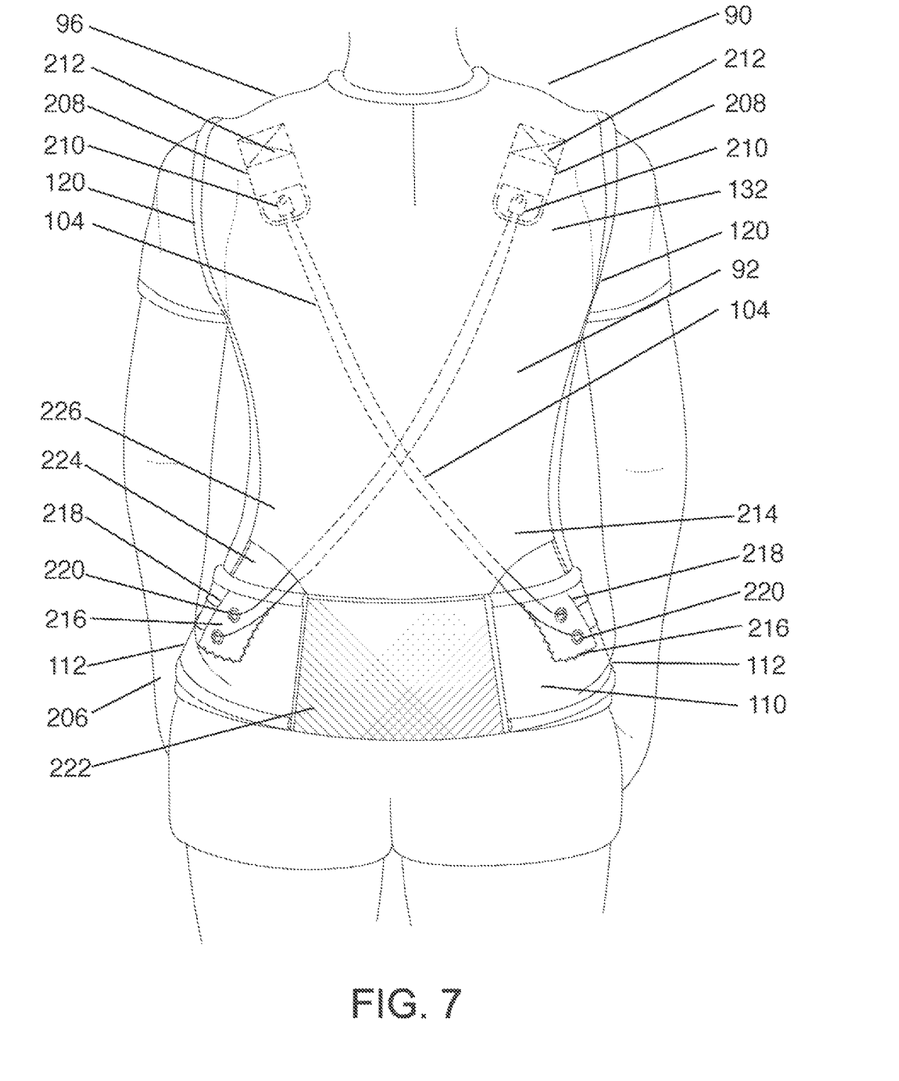
FIG. 7 is a rear elevational view of a specific preferred embodiment of the present invention.

FIGS. 1 and 2 show a front and rear elevational view of a preferred embodiment of the present invention, wherein the device is specifically configured to improve the upper torso alignment of a user. In this particular embodiment shown in FIGS. 1 and 2, the device is modular. The modular device preferably comprises a scapular stabilization brace 90. The scapular stabilization brace 90 typically includes a garment 92 configured to envelop at least a portion of the user's torso. The garment 92 is preferably has an inner and an outer surface, a front side 94, a back side 96, and opposing lateral sides, wherein the front side comprises a chest portion 98 and the back side 96 comprises a back portion 100. The garment as designed herein, typically comprises opposing shoulder portions 102.

Advantageously, the scapular stabilization brace 90 further comprises a pair of tension straps 104 fixed positionally to and in contact with the front side 94 and the back side 96 of the garment 92. While the garment 92 is being worn by the user, the tension straps 104 are releasably secured to—and extend from—alternate sides 112 of the upper front torso of a user. Originating from its respective point of attachment on opposing sides of the upper front torso, each strap 104 extends rearward over said opposing portions of the upper torso (adjacent to a respective shoulder of the user), and then proceeds diagonally toward opposing sides of the user's lower torso, such that substantially the entire length of each tension strap 104 is in direct contact with the outer surface of the garment 92, and such that the tension straps 104 cross over each other near the middle of the user's back.

Preferably, the pair of tension straps 104 are comprised of extendable straps which are releasably secured to each of the front 94 and back 96 portions of the garment 92, so that they may be adjusted to fit the garment 92 to a particular user and/or address any particular needs of the user. More preferably, the tension straps 104 include one or more securing members 116 mounted on each one of the extendable tension straps 104.

In an optional alternative embodiment, the scapular stabilization brace 90 does not include the underlying garment 92. In this alternative embodiment, the strapping system as disclosed above also improves the upper torso alignment of the user.

The preferred embodiment further includes a second brace 106, wherein the second brace comprises an inner 140 and an outer surface 130, a front side 108, a back side 110, and opposing lateral sides 112. The front side 108 of the second brace comprises an abdominal portion 128 and the back side comprises a sacral, lumbar and lower thoracic portion 138. Preferably, the front 108 and back portions 138 are releasably secured to each other in order to encircle the lower torso of the user and increase the compression applied to the user's lower torso.

The scapular stabilization brace 90 and second brace 106 are (optionally) releasably coupled to each other to form the modular design. As used herein, the term modular refers to the multi-component aspect of a preferred embodiment of the device. In alternate embodiments, the device comprises a single component wherein the dynamic scapular stabilization brace 90 is fixed to the static second brace 106. As used herein, the term dynamic refers to an active restraint/strapping system; as opposed to the static support provided by the LSO brace 106. The dynamic brace 90 recruits specific muscle group activation (contraction and relaxation) and sequence these activations to properly align the scapula. The dynamic strapping mechanism applies specific, directional forces to the body that guides the proper positioning of the bones during movement. The dynamic brace 90 is designed to apply specific, directional forces to the body to improve the anatomical alignment of the pelvis, spine, scapula, and arm (and cranium). This mechanical effect guides (not restricts) the proper positioning of the bones during movement.

The dynamic scapular stabilization brace 90 also applies compressive forces to the body that stimulates the sensory receptors in the skin and muscles to send impulses (messages) to the brain regarding changes in position and the movement that the muscles have accomplished (proprioception). This sensory information is utilized to vary muscle tension in response to the specific, directional forces produced by the dynamic scapular stabilization brace 90. Mechanical and sensory cues, therefore, train the shortened muscles to elongate, and elongated muscles to shorten resulting in the balance of muscular tension across the body or a joint and enhanced anatomical alignment.

The device of the present invention is further configured to increase the potential of a subject to produce force and to concurrently reduce clinical symptoms associated with poor anatomical alignment. As clinical symptoms subside, the subject becomes more dependent upon his or her own muscles for support and movement. When increased muscular demand is combined with muscular balance and joint alignment, the result is an increase in muscular strength and function in a subject.

Preferably, according to FIGS. 1-2, the releasable coupling comprises: a pair of guide loops 114 symmetrically disposed on opposing lateral sides of the second brace 106, said guide loops 114 being disposed to receive said extendable straps 104 of said scapular stabilization brace 90 there through. More preferably, said extendable straps 104 are configured to extend out of LSO strap aperture 134 through said directional guide loops 114 along opposing latitudinal planes until they converge at said front portion of the second brace 106. Most preferably, said front portion 108 of said second brace 106 further comprises a securing member 116 for said extendable straps 104, thereby securing each of said extendable straps 104 to the front portion 108 of the second brace 106 and releasably securing the scapular stabilization brace 90 to the second brace 106. Alternatively, the extendable straps 104 may be releasably secured to the lower abdominal portion of the user.

In an alternately preferred embodiment, the present invention is directed to a static and dynamic upper body and trunk neuromuscular training device, the device comprising: a scapular stabilization brace 90 and a lumbar-sacral orthosis ("LSO brace") 106. Preferably, the scapular stabilization brace 90 comprises a dynamic sagittal strapping system 104. According to various embodiments herein, the LSO brace 106 is coupled to the scapular stabilization brace 90. Preferably, the device is configured to externally rotate and retract a user's first and second scapula to create a posterior scapular tilt by bringing a thoracic spine posterior (increasing the scapular carrying angle), align and/or center the user's first and second glenohumeral articulation, stabilize the user's thoracic region of the spine to maintain the natural curve (thoracic kyphosis) of the thoracic vertebrae and restrict the mobility of the trunk, and stabilize the user's lumbar region of the spine to maintain the natural curve (lumbar lordosis) of the lumbar vertebrae and restrict the mobility of the trunk.

Preferably, the scapular stabilization brace 90 in the above embodiment comprises a garment 92 configured to envelop at least a portion of the user's upper torso, the garment 92 having an inner and an outer surface, a front side 94, a back side 96, and opposing lateral sides, wherein the front side 94 comprises a chest portion 98 and the back side 96 comprises a back portion, and the LSO brace 106 comprises an inner and an outer surface, a front side 108, a back side 138, and opposing lateral sides 112, wherein the front side 108 comprises an abdominal portion and the back side comprises a sacral, lumbar and lower thoracic portion, the front 108 and back portions 110 encircling the lower torso of the user and increasing compression applied to the user's lower torso. Advantageously, the garment 92 in various embodiments is preferably further defined by opposing shoulder portions 102 extending about the garment 92. More preferably, in various embodiments, substantially the entire length of each tension strap 104 is in direct contact with the outer surface of the garment 92 such that the tension straps 104 cross over one another near the middle or upper portion 132 of the user's back. Most preferably, said pair of tension straps 104 comprise extendable straps which are releasably secured to each of the front 94 and back portions 96 of said garment 92, such that they may be adjusted to fit the garment 92 to a particular user and to address particular needs of the user, one or more securing members being mounted on each one of the extendable tension straps 104.

In various preferred embodiment, the extendable straps 104 are optionally (but preferably) configured to extend through said directional guide loops 114 along opposing latitudinal planes until they converge at said front portion 108 of the LSO brace 106, wherein said front portion further comprises a securing member for said extendable straps 104, thereby securing each of said extendable straps 104 to the front portion of the second brace 90, thereby securing the first (dynamic) brace, e.g., the scapular stabilization brace, to the second (static) LSO brace 106.

More preferably, the device is configured to dynamically strengthen the user's muscles adjacent to the scapula and thoracic spine through patterns of serial muscle activation, and to reduce the load on the user's cervical region of the spine. In alternate embodiments, the device is configured to supply transcutaneous nerve stimulation to user-selected regions of the upper and/or lower torso. In the same or similar embodiments, the device(s) of the present invention are configured to supply heat and/or cold to user-selected regions of the upper or lower torso.

In this embodiment, the scapular stabilization brace preferably comprises a garment 92 configured to envelop at least a portion of the user's torso, the garment having an inner and an outer surface, a front side 94, a back side 96, and opposing lateral sides, wherein the front side 94 comprises a chest portion 98 and the back side comprises a back portion 100. In the same or similar embodiments, the LSO brace comprises an inner and an outer surface, a front side 108, a back side 110, and opposing lateral sides 112, wherein the front side 108 comprises an abdominal portion and the back side 110 comprises a sacral, lumbar and lower thoracic portion, the front and back portions encircling the lower torso of the user and increasing the compression applied to the user's lower torso. More preferably the LSO brace 106 comprises an LSO brace tightening member 136, configured to control the degree of compression applied by the LSO brace 106 to the user's torso. In various embodiments, the LSO brace tightening member 136 preferably comprises a lacing system. Preferably, the LSO brace 106 further comprises an LSO tightening strap 124, the LSO tightening strap 124 is configured to adjust the amount of compression controlled by the LSO brace tightening member 136, when pulled by a user. More preferably, the LSO tightening strap 124 is disposed on one of the opposing lateral sides 112 of the LSO brace 106 and removably attached to the front side 108 of LSO brace 106. Most preferably, the LSO tightening strap 124 which are extendable and releasably secured to the front side of the 108 of the LSO brace 106, such that the LSO tightening strap 124 may be adjusted to the needs of the user, each LSO tightening strap 124 comprising one or more LSO securing members 126 configured to secure the LSO tightening strap 124 in place after adjustment.

More preferably, the device set forth in various preferred embodiments is further configured to counteract pathological movement of the scapula.

In alternative embodiments, the above device is optionally configured to supply and include transcutaneous nerve stimulation, heat, and/or cold to user-selected regions of the upper and/or lower torso.

FIGS. 3-6 show a front and elevational view of an additional preferred embodiment of the present invention. In FIGS. 3-6, a user is shown adjusting and securing a preferred embodiment of the invention. As shown in FIGS. 3-7, the device preferably comprises a waist member 206 preferably comprising material having inner 130 and an outer surface 140, and opposing distal ends 122. More preferably, the opposing distal ends 122 preferably releasably secured to one another in order to encircle the lower torso of the user and increase the amount compression force applied to the user's lower torso. Preferably the waist member 206 when worn by a user forms a front side 108 on the front of the user, and a back side 110 positioned on the back side of the torso of the user. When worn by the user, the waist member preferably comprises opposing lateral sides 112 positioned in close proximity to the sides of the user's torso. Advantageously, in this embodiment, the opposing distal ends 122 are releasably secured to one another, anchoring the waist member 206 to the user by encircling the user's lower torso.

Additionally, as shown in FIGS. 3-7, the device preferably comprises a waist member 206 and a scapular stabilization brace 90. Preferably the scapular stabilization brace 90 comprises a garment 92, which envelops at least a portion of the user's torso when it is worn by the user. Preferably, the garment 92 has a front side 94, and a back side 96. The front side of the garment 96 preferably comprises a chest portion 98 and the back side 96 preferably comprises an upper back portion 132. The scapular stabilization brace 90 more preferably comprises a pair of tension straps 104 each affixed to opposing lateral sides of the upper back portion 132 of the garment 92. More preferably, when the garment 92 is being worn by the user, each of the pair of tension straps 104 diagonally extends toward opposing sides of the user's lower torso and through a pair of directional guide loops 114, which are disposed on the opposing lateral sides 112 of the waist member 206 and removably attached to the front side of the waist member. Most preferably, the device is modular, the scapular stabilization brace 90 being releasably coupled with the waist member 206.

In one particular embodiment, the waist member 206 may include an LSO brace 206. The front side of the LSO brace 206 preferably comprises an abdominal portion 128 and the back side 110 preferably comprises a sacral, lumbar and lower thoracic portion 138.

Additionally, according to various preferred embodiments, the device may preferably be applied and worn by the user to improve the upper torso alignment.

According to various preferred embodiments the device preferably comprises a waist member 206 to anchor the waist member 206 to and encircle the lower torso of the user and a scapular stabilization brace 90. Preferably, the waist member 206 comprises a main body 222 and opposing distal ends 122. More preferably, the opposing distal ends 122 of the waist member 206 preferably comprise non-flexible material and the main body 222 of the waist member 206 preferably is a compression strap. More preferably the opposing distal ends 122 of the waist member 206 are releasably secured to one another. Most preferably the opposing distal ends 122 are interconnected using a hook-and-loop fastener material.

The scapular stabilization brace 90 preferably comprises a garment 92 having a back side 96 made up of an upper back portion 132 and a lower back portion 214. The garment 92 preferably comprises a stretchable material. More preferably, the lower back portion 214 of the garment 92 is non-removably attached to the main body 222 of the waist member 206. The back side 96 of the garment 92 preferably comprises an inner garment layer 224 and an outer garment layer 226 on the back side 96, both of which, more preferably, span the entire back side 96 of the garment 92. Most preferably, the outer garment layer 226 substantially covers the inner garment layer 224.

The scapular stabilization brace 90 preferably comprises a pair of tension straps 104. The tension straps 104 preferably comprise non-elastic chords. Each tension strap is preferably affixed to opposite lateral sides of the upper back portion 132 of the inner garment layer 224. More preferably, the portion of the tension straps 104 disposed along the back side 96 of the garment 92 are hidden between the inner 224 and outer garment layer 226 of the back side of the garment 92. Most preferably, while the garment is being worn by the user, each tension strap 104 diagonally extends toward opposing sides of the user's lower torso and more preferably passing through strap orientation members 216 preferably disposed opposite lateral sides of the waist member 206 and removably attached to the front side 108 of the waist member. More preferably the tension straps 104 are configured to cross over one another near the middle of the user's back and extend through eyelets 220 disposed on the surface of the strap orientation member 216, which is preferably attached to the waist member 206 such that each strap orientation member 216 forms a pocket with an opening 218 between the waist member 206 and the strap orientation member 216. The tension straps 104 passing through the eyelet pairs 220 and extending from the respective openings 218 of the pockets along opposing latitudinal planes.

Preferably, according to various embodiments, the pair of tension straps 104 are each extendable. More preferably the tension straps 104 and releasably secured to each of the front 94 and back sides 96 of the garment such that the user may adjust the tension straps 104 to the needs of the user. Most preferably each tension strap 104 preferably comprises one or more securing members 116 configured to secure the tension strap 104 in place after the user has adjusted the scapular stabilization brace 90.

Preferably, the tension straps are configured to extend through the strap orientation members 216 along opposing latitudinal planes. More preferably, the tension straps 104 are configured extend along opposing latitudinal planes until they converge at the front side 108 of the waist member 206. Most preferably, the front side 108 of the waist member 206 preferably further comprises a securing mate for the tension strap 104 securing members 116. Each tension strap 104 securing member 116 is preferably secured to the front side of the waist member 206 using the securing member mate. More preferably, the tension strap 104 securing members 116 and the waist member 206 securing mate together comprise a hook-and-loop fastener material to secure the tension strap 104 securing members to the waist member 206 securing mate.

The scapular stabilization brace 90 preferably comprises strap attachment members 208 configured to slidably secure tension straps 104 to opposite lateral sides of the upper back portion 132 of the inner garment layer 224. More preferably, the tension strap attachment members 208 each preferably comprise a strap housing member 210. The strap housing members 210 each preferably comprise two apertures through which the tension straps 104 slidably move. The configuration of the strap attachment members 208, allows for greater flexibility from the device to respond to the movements of the user. Most preferably the strap attachment members 208 each comprise a piece of tension distribution material 212 attached to the strap housing member 210, wherein a portion of each tension distribution material 212 is attached to opposing lateral sides of the upper back portion 132 of the inner garment layer 224.

In an alternate preferred method of use, the present invention comprises a method for improving the upper torso alignment of a user, applying to a user the device according to various preferred embodiments as described above and adjusting the tension straps 104 to improve the upper torso alignment of the user.

Upon reading the teachings of this specification, those with ordinary skill in the art will appreciate that, under certain circumstances, considering issues such as changes in technology, user requirements, etc., a variety of fastening devices may be used to "fix," "secure", "releasably secure", and/or "releasably couple" (as those words are used herein) one or more components of the present invention. These fastening devices may include one or more of the following: adhesives, bolts, buckles, clasps, latches, locks, screws, snaps, clamps, connectors, couplings, ties or other fastening means yet to be developed.

Likewise, upon reading the teachings of this specification, those with ordinary skill in the art will appreciate that, under certain circumstances, considering issues such as changes in technology, user requirements, etc., a variety of fastening devices, such as adhesives, belts, bolts, buckles, clasps, latches, locks, screws, snaps, clamps, connectors, couplings, ties or other fastening means yet to be developed may be used in lieu of—or in conjunction with—the "straps," "tension straps," and/or "extendable straps" (as those words are used herein).

The present invention also includes methods of use. One such (preferred) method of use comprises a static and dynamic upper body and trunk neuromuscular training method for improving alignment of the upper quadrant of the kinetic chain of a subject by improving spinal and shoulder alignment, scapular kinematics and proprioception, said method comprising the steps of:

(a) externally rotating and retracting a first and second scapula to create a posterior scapular tilt by bringing a thoracic spine posterior thereby increasing the scapular carrying angle;

(b) aligning and/or centering a first and second glenohumeral articulation;

(c) statically and/or dynamically stabilizing a thoracic region of the spine to maintain the natural curve (thoracic kyphosis) of the thoracic vertebrae and restrict the mobility of the trunk;

(d) statically stabilizing a lumbar region of the spine to maintain the natural curve (lumbar lordosis) of the lumbar vertebrae and restrict the mobility of the trunk;

(e) dynamically strengthening the muscles adjacent to the scapula and thoracic spine through patterns of serial muscle activation; and (f) reducing the load on the cervical region of the spine.

In an alternate preferred method of use, the present invention comprises a method for treating or reducing the risk of a shoulder injury in a subject comprising the steps of:

(a) externally rotating and retracting a first and second scapula to create a posterior scapular tilt by bringing a thoracic spine posterior thereby increasing the scapular carrying angle;

(b) aligning and/or centering a first and second glenohumeral articulation;

(c) statically and/or dynamically stabilizing a thoracic region of the spine to maintain the natural curve (thoracic kyphosis) of the thoracic vertebrae and restrict the mobility of the trunk;

(d) statically stabilizing a lumbar region of the spine to maintain the natural curve (lumbar lordosis) of the lumbar vertebrae and restrict the mobility of the trunk;

(e) dynamically strengthening the muscles adjacent to the scapula and thoracic spine through patterns of serial muscle activation; and (f) reducing the load on the cervical region of the spine.

In an additional embodiment, the present invention further encompasses a static and dynamic upper body and trunk neuromuscular training device for improving alignment of the upper quadrant of the kinetic chain by improving spinal and shoulder alignment, scapular kinematics and proprioception, said device comprising:

(a) means for externally rotating and retracting a first and second scapula to create a posterior scapular tilt by bringing a thoracic spine posterior (increasing the scapular carrying angle);

(b) means for aligning and/or centering a first and second glenohumeral articulation;

(c) means for statically and/or dynamically stabilizing a thoracic region of the spine to maintain the natural curve (thoracic kyphosis) of the thoracic vertebrae and restrict the mobility of the trunk;

(d) means for statically stabilizing a lumbar region of the spine to maintain the natural curve (lumbar lordosis) of the lumbar vertebrae and restrict the mobility of the trunk;

(e) means for dynamically strengthening the muscles adjacent to the scapula and thoracic spine through patterns of serial muscle activation; and (f) means for reducing the load on the cervical region of the spine.

Preferably, various embodiments described hereinabove produce intracavity pressure to reduce the load on the intervertebral disk. More preferably, according to various embodiments described hereinabove further comprises elevating the acromion to avoid impingement and compression of the rotator cuff. Most preferably, according to various embodiments described hereinabove further comprise a means to counteract pathological movement of the scapula.

Although applicant has described applicant's preferred embodiments of this invention, it will be understood that the broadest scope of this invention includes modifications. Such scope is limited only by the below claims as read in connection with the above specification. Further, many other advantages of applicant's invention will be apparent to those skilled in the art from the above descriptions and the claims below.

We claim:

1. A device for improving an upper torso alignment of a user having a back and torso, including the upper torso and a lower torso, the device comprising:

(a) a waist member, wherein the waist member comprises a main body, an inner and an outer surface, and opposing distal ends, wherein when worn by the user, the waist member comprises a front side, a back side, and opposing lateral sides, and the opposing distal ends are releasably secured to one another in order to anchor the waist member to and encircle the lower torso of the user; and (b) a scapular stabilization brace, wherein the scapular stabilization brace comprises a garment configured to envelop at least a portion of the user's torso, the garment having, a front side, and a back side, wherein the front side of the garment comprises a chest portion and the back side of the garment comprises an upper back portion, a lower back portion, an inner garment layer, and an outer garment layer that substantially covers the inner garment layer, wherein the scapular stabilization brace further comprises a pair of tension straps each having a first tension strap end attached to opposing lateral sides of the upper back portion of the inner garment layer, the pair of tension straps each being positioned between the inner garment layer and the outer garment layer, wherein each of the pair of tension straps extends diagonally across the back side of the garment, without being directly secured to each other, towards opposite sides of the lower back portion of the garment; wherein each of the pair of tension straps extend through a separate tension strap orientation member pair of disposed on the opposing lateral sides of the waist member; the tension straps each being removably attachable to the front side of the waist member at a second tension strap end.

2. The device of claim 1, wherein the pair of tension straps which are extendable and releasably secured to each of the front and back sides of the garment, each tension strap comprising one or more tension strap securing members configured to secure the tension strap in place after adjustment.

3. The device of claim 2, wherein the tension straps are configured to extend through the tension strap orientation members along opposing latitudinal planes until the second tension strap ends converge at the front side of the waist member, wherein the front side of the waist member further comprises a securing mate for the tension strap securing members, wherein each tension strap securing member may be secured to the front side of the waist member using the securing mate.

4. The device of claim 3, wherein the tension strap securing members and the securing mate together comprise a hook-and-loop fastener material to secure the tension strap securing members to the securing mate.

5. The device of claim 1, wherein the scapular stabilization brace comprises strap attachment members configured to slidably secure tension straps to opposing lateral sides of the upper back portion of the inner garment layer.

6. The device of claim 5, wherein the strap attachment members each comprise a strap housing member, wherein the strap housing members each comprise a first and second aperture through which the tension straps slidably move to adjust the device.

7. The device of claim 6, wherein the strap attachment members each comprise a piece of tension distribution material attached to the strap housing member, wherein a portion of each tension distribution material is attached to opposing lateral sides of the upper back portion of the inner garment layer.

8. The device of claim 1, wherein each tension strap is adapted to cross over one another near a middle of the user's back.

9. The device of claim 1, wherein the opposing distal ends of the waist member are releasably secured to one another using a hook-and-loop fastener.

10. The device of claim 1, wherein the opposing distal ends of the waist member comprise non-flexible material and the main body of the waist member comprises a compression strap.

11. The device of claim 1, wherein the lower back portion of the garment is non-removably attached to the main body of the waist member.

12. The device claim 1, wherein the tension straps comprise non-elastic chords.

13. The device of claim 1, wherein the garment of the scapular stabilization brace is made of a stretchable material.

14. The device of claim 1, wherein the tension strap orientation members are attached to the waist member such that each tension strap orientation member forms a pocket on the waist member, each pocket comprising an opening and a pair of eyelets disposed on a surface of each pocket, wherein the tension straps are configured to extend through the eyelets and through the opening of the pocket along opposing latitudinal planes.

15. A device for improving an upper torso alignment of a user having a back and torso, including the upper torso and a lower torso, the device comprising:
   (a) a waist member, wherein the waist member comprises a main body, an inner and an outer surface, and opposing distal ends, wherein when worn by the user, the waist member comprises a front side, a back side, and opposing lateral sides, and the opposing distal ends are releasably secured to one another in order to anchor the waist member to and encircle the lower torso of the user; and
   (b) a scapular stabilization brace, wherein the scapular stabilization brace comprises a garment configured to envelop at least a portion of the user's torso, the garment having, a front side, and a back side, wherein the front side of the garment comprises a chest portion and the back side of the garment comprises an upper back portion, a lower back portion, an inner garment layer, and an outer garment layer that substantially covers the inner garment layer, wherein the scapular stabilization brace further comprises a pair of tension straps each having a first tension strap end attached to opposing lateral sides of the upper back portion of the inner garment layer, the pair of tension straps each being positioned between the inner garment layer and the outer garment layer, wherein each of the pair of tension straps extends diagonally across the back side of the garment towards opposite sides of the lower back portion of the garment; wherein each of the pair of tension straps extend through a separate tension strap orientation member disposed on the opposing lateral sides of the waist member; the tension straps each being removably attachable to the front side of the waist member at a second tension strap end;
   wherein, while the garment is being worn by the user, the first tension strap end of each of the pair of tension straps is attached at a respective scapula of the user.

16. The device of claim 15, wherein the pair of tension straps which are extendable and releasably secured to each of the front and back sides of the garment, each tension strap comprising one or more tension strap securing members configured to secure the tension strap in place after adjustment.

17. The device of claim 16, wherein the tension straps are configured to extend through the tension strap orientation members along opposing latitudinal planes until the second tension strap ends converge at the front side of the waist member, wherein the front side of the waist member further comprises a securing mate for the tension strap securing members, wherein each tension strap securing member may be secured to the front side of the waist member using the securing mate.

18. The device of claim 15, wherein the scapular stabilization brace comprises strap attachment members configured to slidably secure tension straps to opposing lateral sides of the upper back portion of the inner garment layer.

19. A device for improving an upper torso alignment of a user having a back and torso, including the upper torso and a lower torso, the device comprising:

(a) a waist member, wherein the waist member comprises a main body, an inner and an outer surface, and opposing distal ends, wherein when worn by the user, the waist member comprises a front side, a back side, and opposing lateral sides, and the opposing distal ends are releasably secured to one another in order to anchor the waist member to and encircle the lower torso of the user; and (b) a scapular stabilization brace, wherein the scapular stabilization brace comprises a garment configured to envelop at least a portion of the user's torso, the garment having, a front side, and a back side, wherein the front side of the garment comprises a chest portion and the back side of the garment comprises an upper back portion, a lower back portion, an inner garment layer, and an outer garment layer that substantially covers the inner garment layer, wherein the scapular stabilization brace further comprises a pair of tension straps each having a first tension strap end affixed to opposing lateral sides of the upper back portion of the inner garment layer, the pair of tension straps each being positioned between the inner garment layer and the outer garment layer, wherein each of the pair of tension straps extends diagonally across the back side of the garment, without being directly secured to each other, towards opposite sides of the lower back portion of the garment; wherein each of the pair of tension straps extend through a separate tension strap orientation member disposed on the opposing lateral sides of the waist member; the pair of tension straps each being removably attachable to the front side of the waist member at a second tension strap end;

wherein, while the garment is being worn by the user, the first tension strap end of each of the pair of tension straps is attached at a respective scapula of the user.

20. The device of claim 19, wherein the tension strap orientation members are attached to the waist member such that each tension strap orientation member forms a pocket on the waist member, each pocket comprising an opening and a pair of eyelets disposed on a surface of each pocket, wherein the tension straps are configured to extend through the eyelets and through the opening of the pocket along opposing latitudinal planes.

* * * * *